United States Patent [19]

Pietzsch

[11] Patent Number: 4,904,877

[45] Date of Patent: Feb. 27, 1990

[54] OPTICAL SCANNING APPARATUS FOR DETECTING FAULTS IN TRANSPARENT MATERIAL WHEREIN THE PLANE OF INCIDENT LIGHT IS ARRANGED AT THE BREUSTER ANGLE TO THE NORMAL TO THE SURFACE

[75] Inventor: Karl Pietzsch, Geretsried, Fed. Rep. of Germany

[73] Assignee: Erwin Sick GmbH Optik-Elektronik, Waldkirch, Fed. Rep. of Germany

[21] Appl. No.: 234,453

[22] Filed: Aug. 19, 1988

[30] Foreign Application Priority Data

Aug. 24, 1987 [DE] Fed. Rep. of Germany ....... 3728210

[51] Int. Cl.⁴ .............................................. G01N 21/88
[52] U.S. Cl. ..................................... 250/572; 250/225
[58] Field of Search ................ 250/560, 561, 570, 571, 250/572, 236; 356/237, 382; 350/6.1

[56] References Cited

U.S. PATENT DOCUMENTS

| | | | |
|---|---|---|---|
| 3,734,624 | 5/1973 | Cornelius | 356/118 |
| 3,994,586 | 11/1976 | Sharkins et al. | 356/73 |
| 4,110,047 | 8/1978 | Takahashi | 356/200 |
| 4,568,835 | 2/1986 | Imamura et al. | 250/572 |
| 4,748,329 | 5/1988 | Cielo et al. | 356/382 |

Primary Examiner—David C. Nelms
Assistant Examiner—William L. Oen
Attorney, Agent, or Firm—Townsend & Townsend

[57] ABSTRACT

An optical scanning apparatus for transparent, substantially flat material comprises a light source (21) and a mirror wheel (22) illuminated by the light beam. The mirror wheel generates a scanning beam which executes a periodic scanning movement in a scanning plane extending obliquely to the surface of the material. The scanning beam generates a scanning light bead on the surface of the material with the scanning light bead moving along a scanning line. A photoelectric light receiving device is arranged at the angle of reflection. The plane of incidence (11) is arranged at the Brewster angle relative to the normal (12) to the surface of the material (13). The light of the scanning beam (14) which executes the periodic scanning movement in the scanning plane (11) is linearly polarized parallel to the surface of the material or perpendicular to the scanning plane (11).

6 Claims, 5 Drawing Sheets

OPTICAL SCANNING APPARATUS FOR DETECTING FAULTS IN TRANSPARENT MATERIAL WHEREIN THE PLANE OF INCIDENT LIGHT IS ARRANGED AT THE BREUSTER ANGLE TO THE NORMAL TO THE SURFACE

The invention relates to an optical scanning apparatus for transparent, substantially flat, plate-like or sheet-like material, the apparatus comprising a light source, a light deflecting device, such as a mirror wheel, illuminated by the light beam generated by the light source, with the light deflecting device generating a scanning beam which executes a periodic scanning movement in a scanning plane extending obliquely to the surface of the material and with the scanning beam generating a scanning light bead on the surface of the material, with the scanning light bead moving along a scanning line and with a photoelectric light receiving device arranged at the angle of reflection.

Known optical scanning apparatuses (for example DE-OS 25 52 331, DE-OS 33 14 620) serve to detect faults which absorb or scatter light, deviations of the work surface from the flat state and also deviations of the web perpendicular to its plane from a normal position, and to make such faults accessible to systematic electrical measurement by appropriate signals at the output of the light receiving device. The light receiving device can consist of a single photomultiplier or of an arrangement of several individual photoreceivers alongside one another. Surface arrays or position sensitive individual photoreceivers can also be used in order to detect deviations of a reflected beam to several sides from a normal position.

Problems in measuring the flatness of the surfaces of transparent material webs however occur because the scanning beam incident on the surface is reflected both at the front side and also at the rear side of the material web, so that two received signals are superimposed in the photoelectric light receiving arrangement and no unambiguous fault signal can any longer be obtained, particularly with different deviations in the flatness of the front side and rear side of the web.

The object underlying the present invention is thus to provide an optical scanning device of the initially named kind with which the deviations in flatness of the front and rear surfaces of the material can be optically derived pointwise and detected in the form of electrical signals.

In order to satisfy this object the present invention provides an arrangement which is characterised in that the scanning plane is arranged at the Brewster angle relative to the normal to the surface of the material; in that the light of the scanning beam which executes the periodic scanning movement in the scanning plane is linearly polarised parallel to the surface of the material; and in that light reflected from the upper side and from the lower side of the web material is differentially detected by the light receiving arrangement by determining angular deviations between the beams reflected from the upper side and from the lower side.

As a result of this construction two laterally displaced reflected beams occur the direction of reflection of which is influenced by deviations of the upper or lower surface of the material from the flat state. If the two reflected beams are for example parallel to one another as a result of surfaces which extend exactly parallel to one another, then they fall at the same point on a position sensitive light receiving arrangement, which can be evaluated as a measure for the parallelism of the two beams. As a result of the position sensitivity of the light receiving arrangement it can also be deduced whether the two displaced reflected beams which extend parallel to one another deviate as a whole from a predetermined normal reflection direction.

If the flatness of the two surfaces however deviate somewhat from one another then the two reflected beams from the front and rear surfaces subtend an angle to one another so that they impinge at different points on the position sensitive light receiving arrangement which can be evaluated for determination of the angle and thus also to detect the relative deviations from flatness. With this method it is thus only the difference in the deviations of the two surfaces from a state of flatness which can be determined.

The optical scanning apparatus of the invention is used in particularly advantageous manner in combination with a classical scanning apparatus which operates in refraction or transmission in as much as a second scanning beam which executes a scanning movement in a steeper scanning plane impinges on the scanning line; and in that a further photoelectric light receiving arrangement is respectively arranged at the angle of reflection $\beta$ of the second scanning beam and/or in its extension.

It this arrangement it is of advantage for the two scanning beams present in the two scanning planes are generated using a partially transmitting mirror from the same light source and the same light deflecting device.

In particular provision should be made that the light receiving arrangements have at least two and preferably however several individual photoreceivers arranged in a specific direction alongside one another.

It is particularly expedient when the individual photoreceivers are arranged as an areal array. The use of a position sensitive individual photoreceiver is also possible.

The present invention also comprises a method of measuring the deviations of the surface of a transparent material from the state of flatness using a scanning device with the method being characterised in periodic light is used which is periodically alternately polarised parallel and perpendicular to the scanning plane; and in that the output signals of the light receiving arrangement are separately evaluated within each period in which a specific state of polarisation exists.

In a preferred arrangement in which the material is continuously moved perpendicular to the scanning line and parallel to its plane, the above method is preferably further characterised in that the material is continuously advanced perpendicular to the scanning line and parallel to its plane, characterised in that the direction of polarisation is periodically changed with a frequency which is so high that practically at each point of the material one measurement takes place with the one direction of polarisation and one measurement takes place with the other direction of polarisation; and in that the deviations of both the lower side and also of the upper side from flatness are derived from the two measurements and indeed either summed or individually.

In these embodiments the light incident on the measuring location on the material is thus polarised parallel to the surface during a first period. In this case a first part of the incident light beam will be reflected at the upper surface and a second part at the lower surface of the material. The two reflected beams can either be separately detected by the light receiving arrangement or as a sum with defined components from the upper and lower surface.

During the next measuring period light is used which is polarised perpendicular to the scanning plane. As a result of the arrangement at the Brewster angle no light is reflected at the upper surface but instead the entire quantity of light penetrates at the angle of refraction fully into the interior of the material web. This light is reflected if the rear side of the web is coated at the rear or lower surface of the material and reaches the light receiving arrangement which can thus also form an electrical signal representative of the angular tilting of the deviation from a state of flatness of the rear side or other error of the material.

A particularly advantageous embodiment of the invention is thus to be seen in the fact that switching is effected in a rapid sequence to and fro between the two polarisation directions and that the light receiving arrangement is synchronised with this switching process via an electronic evaluation circuit in such a way that the two measurement procedures are separated in the electronic evaluation circuit. The rapid change-over between the two directions of polarisation can for example be realised by a rapidly rotating polarisation filter. One can also use two cyclically operating light sources with directions of polarisation arranged perpendicular to one another whose light beams can be deflected into the same beam path.

The use of light polarised parallel to the surface for fault inspection in film emulsions is admittedly already known (US-PS 37 34 624) however, an attempt is made there to suppress the beam component which is reflected at the lower surface of the emulsion so that, in contrast to the invention, it is not used for the measurement of angular faults of the upper and lower surfaces relative to one another.

Whereas the angle of incidence of the scanning beam in a classical fault scanning apparatus lies at approximately 10° the angle of incidence of the polarised scanning beams, i.e. the Brewster angle, lies for example at 56°.

In the simplest case the generation of polarised light can take place by the use of a linear polarisation filter in unpolarised light.

It is however also possible to use to circularly polarised light and to convert this into a suitably directed linearly polarised light by a quarter wave plate.

Furthermore it is possible from the outset to use a polarised light in one of the two preferential directions and to rotate its direction of polarisation periodically through 90° by a half wave plate. The polarised light can also be generated by filtering circularly polarised light.

In the event that the scanning apparatus of the invention is combined with a classical scanning apparatus, in which the light incidence at the Brewster angle is effected by a partially transmitting mirror, then the larger optical path in the scanning beam incident at the Brewster angle is not problematic because the angular tilting errors which are to be found here are mainly very much larger in area than defects in the material which are to be found, for example scratches. The scanning beam, which is incident at the Brewster angle, may therefore also be somewhat defocussed on impinging onto the surface of the work material.

The Brewster angle is computed in known manner in accordance with the formula:

$$\tan\alpha = (n_1/n_2)$$

where $n_1$ is the refractive index above the material, i.e. the the refractive index of air ($=1$), whereas $n_2$ is the refractive index of the material.

The invention will now be described in the following by way of example and with reference to the drawings in which are shown:

FIG. 1 a schematic perspective illustration of a first embodiment of an optical scanning apparatus in accordance with the invention, FIG. 1a a schematic illustration of the beam path with light incidence at the Brewster angle and using light polarised parallel to the material surface, FIG. 2 a second embodiment with a telecentric beam path, FIG. 3 a schematic block diagram of a preferred evaluation circuit for the embodiment of FIG. 2, FIG. 4 a sideview of an optical scanning apparatus in accordance with the invention combined with a classical scanning apparatus, FIG. 5 a schematic block circuit diagram of a first advantageous evaluation circuit for the embodiment of FIG. 4, and FIG. 6 a schematic block circuit diagram of another advantageous evaluation circuit for the embodiment of FIG. 4.

In accordance with FIG. 1 a laser 21 illuminates a mirror wheel 22 rotating in the direction of the arrow via a beam broadening optical system 29 and a plane deflecting mirror 30. The mirror wheel 22 forms a scanning beam 14 in a sector-like scanning beam plane 11 and the scanning beam generates a sharp light bead 16 on the surface of a transparent web-like material 13 arranged beneath the mirror wheel. This sharp light bead 16 periodically scans the surface along a scanning line 15 in the direction of the arrow.

The material 13 is continuously advanced in the direction of the arrow L and indeed at a speed such that in practice all points of the work surface are detected once by the light bead 16, through the linewise scanning of the surface of the material 13 transverse to the direction of advance. A linear polariser 31 is arranged close to the mirror wheel 22 within the plane of incidence 11 and polarises the light coming from the laser 21 linearly parallel to the scanning line 15. The angle of incidence α which the scanning plane 11 includes with the normal 12 to the material 13 is the same as the Brewster angle.

A light receiving arrangement 17 is provided at the angle of reflection α to the normal 12 and includes a strip-like concave mirror 32 which gathers the light reflected from the surface of the web material 13 and forms an image of the surface of the mirror wheel 22 on a photoreceiver array via a strip-like plane deflecting mirror 33. The photoreceiver array comprises a central single photoreceiver 23 and further individual photoreceivers 24, 25, 26 and 27 arranged around it.

When the surface of the web material 13 is undisturbed, i.e. faultfree, the sharp light bead 16 located on the surface of the mirror wheel 22 is imaged onto the central single photoreceiver 23, so that the attached electronic evaluation circuit 28 transmits a signal representative of an undisturbed faultfree web surface.

If the surface of the web material 13 is in contrast tilted in one or the other direction at the position where the light bead 16 instantaneously strikes it, i.e. if it deviates in one or other direction from the desired flatness, then the image of the light bead on the mirror wheel 22 reaches one of the adjacent individual photoreceivers 24, 25, 26 or 27, whereupon the electronic evaluation circuit 28 forms a corresponding angular deviation signal, from which conclusions can be drawn concerning the nature and the degree of unevenness of the web surface at this position.

Figure 1A:
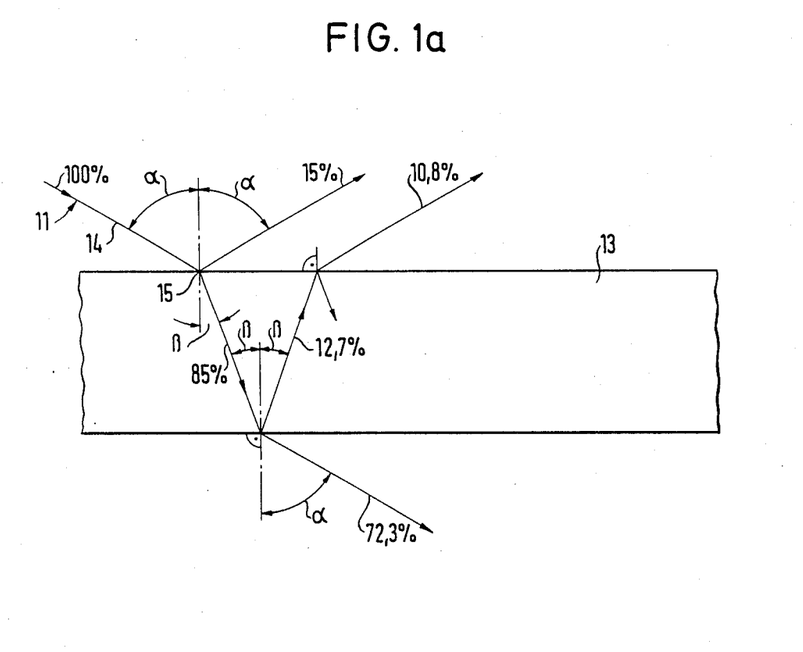

FIG. 1a shows to a greatly enlarged scale, a cross-section through the board-like or sheet-like material 13 of FIG. 1, with the plane of cutting standing perpendicular to the scanning line 15. The polarisation direction of the scanning beams 14 extends parallel to the scanning plane 11 and the surface of the material 13.

The light intensity of the scanning beam 14 incident on the surface of the material 13 is designated with 100%. 15% of the light intensity is reflected at the angle of reflection $\alpha$ at the surface of the material 13. 85% of the light intensity will be refracted at the angle of refraction $\beta$ into the interior of the material 13 where it then strikes the lower or rear surface of the material 13. There 72.3% of the light intensity leaves the material 13, whereas 12.7% is reflected back at the angle of reflection $\beta$ to the upper surface of the material 13. Of this light 10.8% of the original light intensity emerges from the upper surface of the material 13. The further reflections indicated only as an arrow within the material 13 are negligible from the point of view of their intensity.

In FIG. 1a it is assumed that the upper surface and the lower surface of the material 13 extend exactly parallel to one another at the position of incidence of the incident scanning beam 14, so that the two emergent beams extend parallel to one another with intensities of 10.8 and 15% respectively. They would be united by the optical arrangement of FIG. 1 onto the central individual photoreceiver 23.

If the two surfaces have errors in flatness while retaining precise parallelism then the two reflected beams with 10.8 and 15% of the intensity will be deflected onto one of the side disposed individual photoreceivers 24, 25, 26 or 27. The fact that only one single individual photoreceiver is illuminated by one light point thus states that the front and rear surface extend precisely parallel to one another at the light impingement positions.

If the front and rear surfaces of the material 13 are not precisely parallel then an angle arises between the reflected beams with 10.8 and 15% light intensity, which for example leads to one beam impinging on the central individual photoreceiver 23, while the other beam impinges on the side photoreceiver 25. From this conclusions can be drawn regarding the angular divergence and thus the deviation from parallelism of the two surfaces of the material 13 at the positions of light incidence. The corresponding evaluations are effected in the electronic evaluation circuit 28, the practical embodiment of which can be, as shown in the block circuit diagram of FIG. 3, which will be described below in conjunction with FIG. 2.

In the following figures the same reference numerals are used to designate components which have counterparts in FIG. 1.

Figure 2:
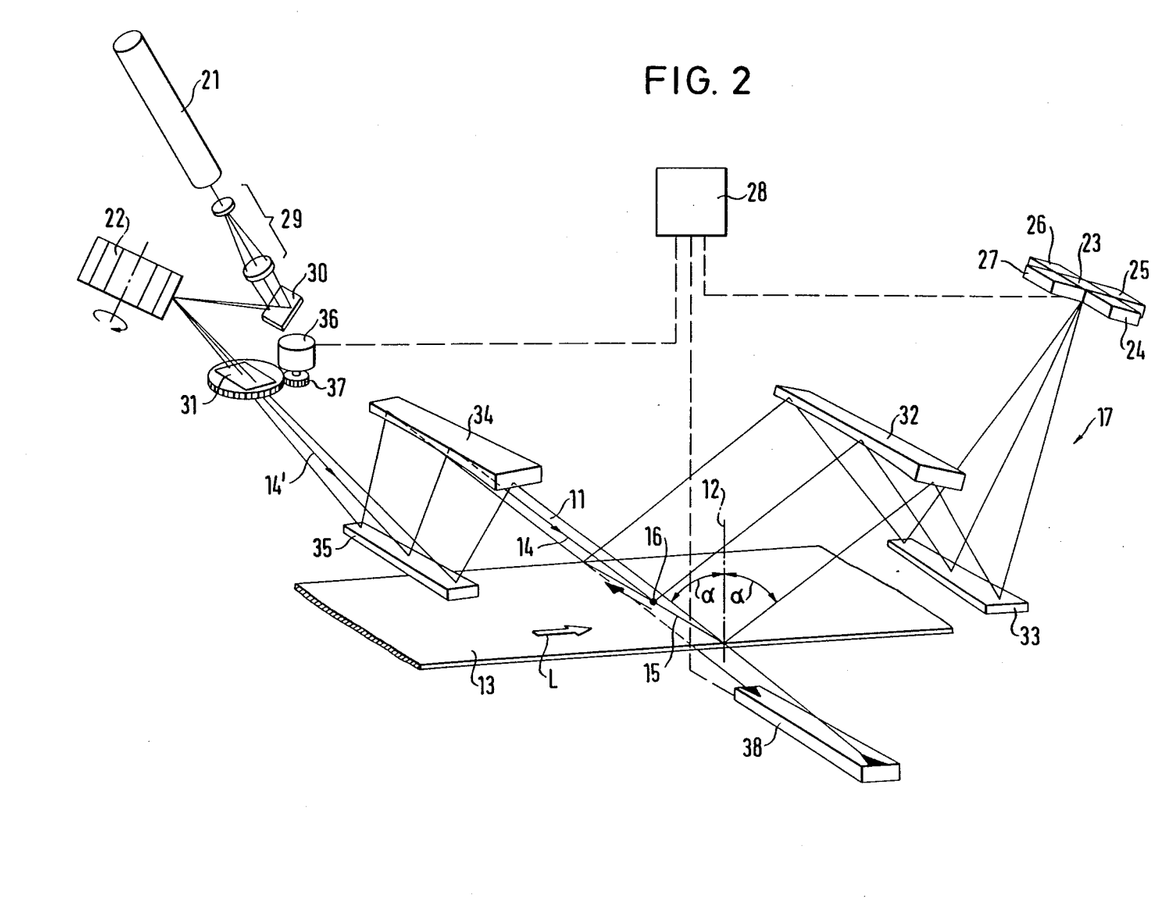

A telecentric beam path is provided in the embodiment of FIG. 2, in distinction to FIG. 1. The light transmitted by the mirror wheel 22 through the polarisation filter 31 is first deflected via a plane deflecting mirror 35 onto a strip-like concave transmitter mirror 34, the focal point of which lies on the surface of the mirror wheel 22. In this way a scanning beam 14 is generated, which on rotation of the mirror wheel 22 is displaced parallel to itself. During this the scanning beam 14 again runs through the scanning plane 11 which extends at the Brewster angle $\alpha$ to the normal to the material 13.

The strip-like concave mirror 32 at the receiver side is so arranged that it concentrates the received light onto the central individual photoreceiver 23 of the photoreceiver array when the surfaces at the position of light incidence extend parallel to one another and are arranged in a desired plane which corresponds to the arrangement of the plane material 13 in FIG. 2. The photoreceiver array 23 to 27 is thus located at the focal point of the strip-like concave mirror 32.

Furthermore it is indicated in FIG. 2, in distinction to FIG. 1, that the polarisation filter 31 is rotatable about an axis which coincides with the central scanning beam 14' and indeed by a motor 36 which for example drives the holder of the polarisation filter 31, which is provided with an outer toothed ring, via a pinion 37, so that the polarisation filter executes a rapid rotary movement. The motor 36 is controlled by the electronic evaluation circuit 28 and transmits an angular position signal to the electronic evaluation circuit 28 which makes it possible for the evaluation circuit 28 to recognise the instantaneous direction of polarisation of the scanning beam 14 and to synchronise with the received signals from the photoreceiver array 23, 24, 25, 26, 27.

A further light receiving arrangement 38 is provided in the extension of the scanning beam 14 behind the material web 13 which receives the total light passed through the web material 13 and converts it into a corresponding electrical signal. The photoelectronic light receiving arrangement 38 can be constructed in similar manner to the photoelectric light receiving arrangement 17 operating in reflection, this is however not illustrated in order to simplify the illustration.

As a result of this construction, when the polarisation filter 32 generates light with a polarisation direction extending parallel to the scanning line 15, light will enter in reflection in accordance with FIG. 1a into the light receiving arrangement 17 and in transmission (72.3% in FIG. 1) into the light receiving arrangement 38. Light receiving arrangement 38 will respond, with a construction corresponding to that of the light receiving arrangement 17 (position sensitive), to wedge errors of the material at the position of light incidence.

Figure 3:
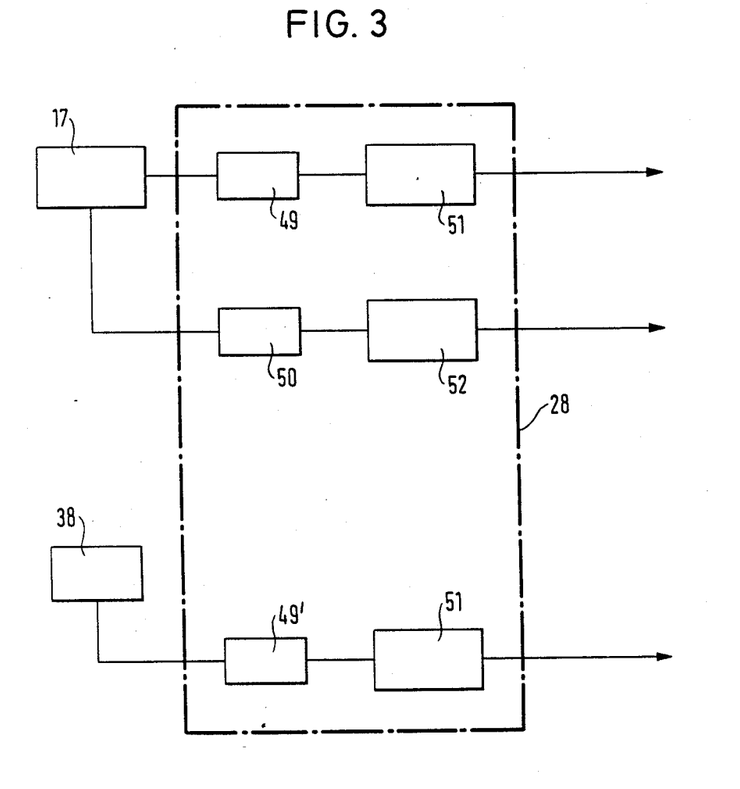

An evaluation circuit for the received signals is shown in FIG. 3 for the case in which the light is polarised parallel to the scanning line 15. The received signals of the light receiving arrangement 17 are transmitted within the electronic evaluation circuit 28 on the one hand to a position sensitive detector circuit 51 and to an error detector circuit 52 via a low pass filter 49 and a recursive filter 50, respectively. The position sensitive detector circuit 51 delivers at its output a signal which corresponds to the sum of the flatness error (angular tilting) at the upper and lower surface of the material web in the region of the point of light incidence. Error signals appear at the output of the fault detector circuit 52 which are representative of defects within the material 13 or on its upper side.

The further light receiving arrangement 38 is connected via a low pass filter 49' to a position sensitive detector circuit 51 so that a signal representative of the wedge angle between the two surfaces at the position of light incidence appears at the output of the detector circuit 51.

The evaluation circuit of FIG. 3 is used when light is used which is always polarised parallel to the surface of the material 13, i.e. when the polarisation filter 31 is not rotating.

Figure 6:
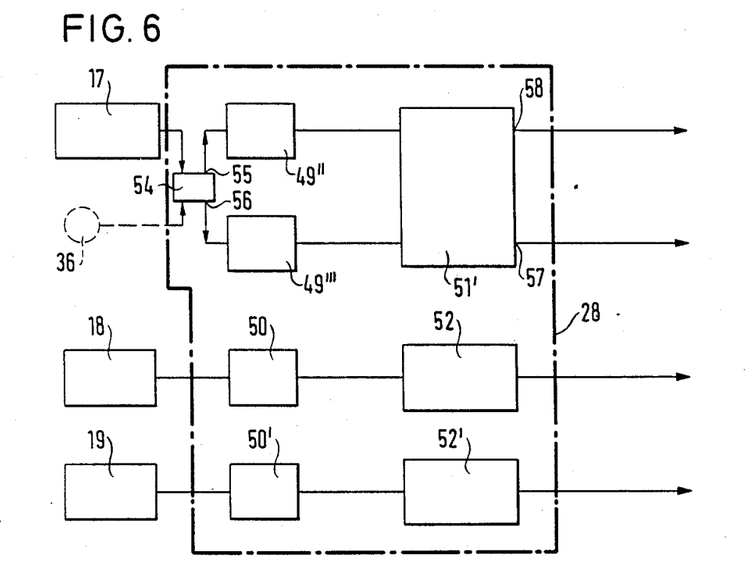

If now the polarisation filter 31 in FIG. 2 is set rotating, so that light which is alternately polarised parallel and perpendicular to the scanning plane comes into action, then evaluation is expediently effected in accordance with the upper circuit diagram in FIG. 6. The output signals are applied within the evaluation circuit 28 to a polarisation direction selection stage 54 which is controlled by the angular position signal derived from the motor 36. Thus a first output signal appears at the output 55 for light which is polarised parallel to the scanning plane 11. A further output signal is available at the output 56 which corresponds to light incidence on the individual photoreceivers 23 to 27 when the light is polarised perpendicular to the scanning plane 11. The two outputs 55, 56 are applied via low pass filters 49", 49‴ to a position sensitive detector 51' which operates as follows:

A fault signal 49" corresponding to the sum of the flatness errors of the front and rear surface is transmitted from the low pass filter 49" to the position sensitive detector 51' The low pass filter 49‴ delivers only a signal representative for the flatness error of the coated rear side of the material 13. In the position sensitive detector circuit 51' these signals are so processed that a signal appears at a first output 57 which is representative of the flatness error of the rear surface of the material 13 and so that a signal appears at the output 58 which is representative for the flatness error of the upper surface of the material 13, which can be derived by difference formation from the signals coming from the low pass filter 49" on the one hand, and from the low pass filter 49‴ on the other hand. The difference signal obtained in this way can also be multiplied by a correction factor.

In this manner it is not only possible to measure the flatness error of the upper and lower surface of the material 13 (FIG. 3 upper circuit diagram), but it is also possible to separately measure the absolute lack of flatness of both the upper and lower surfaces.

Figure 4:
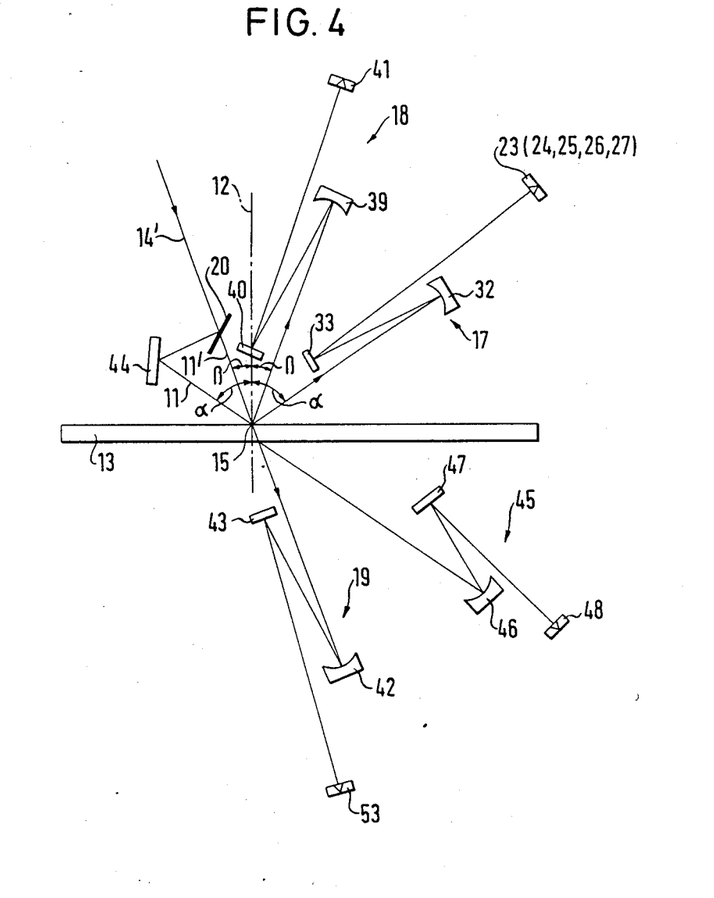

FIG. 4 schematically shows the combination of an optical scanning apparatus in accordance with the invention operating with polarised light at the Brewster angle with a classical scanner.

A transmitting scanning device such as is shown in FIGS. 1 and 2 first generates a primary scanning beam 14' which executes a scanning movement perpendicular to the plane of the drawing of FIG. 3. This primary scanning beam 14' impinges at an angle $\beta$ onto the surface of the web material 13 which is relatively steep (for example 10°) and is in any case substantially smaller than the Brewster angle $\alpha$. A photoelectric light receiving arrangement 18 is located at the reflection angle $\beta$ comprising a strip-like concave mirror 39 perpendicular to the plane of the drawing, a deflecting mirror 40 and a photoreceiver 41 consisting of one or more individual photoreceivers.

A further photoelectrical light receiving arrangement 19 is furthermore provided in the extension of the primary scanning beam 14' and has a strip-like concave mirror 42, a plane deflecting mirror 43 and also a photoreceiver 53 consisting of one or more individual photoreceivers.

Faults of the web material 13 in reflection or transmission can be determined in the classical manner with the arrangement described here.

A partially transmitting mirror 20 is located within the primary scanning beam 14' and the deflects a part of the transmitted light to a plane deflecting mirror 44 which reflects the incident light at an angle to the scanning line 15 of the primary scanning beam 14' in such a way that the second plane of incidence 11 which is formed in this way impinges onto the surface of the web material 13 at the Brewster angle $\alpha$.

The photoelectric light receiving arrangement 17 is again arranged at the reflection angle $\alpha$ in analogous manner to the arrangement of FIGS. 1 and 2.

Moreover, a further photoelectric light receiving arrangement 45 is provided in the extension of the plane of incidence 11 beneath the web material 13 and again includes a strip-like concave mirror 46, a strip-like plane deflecting mirror 46 and a photoreceiver 48 consisting of one or more individual photoreceivers. In this way one can, using one and the same scanner, determine errors in the classical manner and can also detect angular tilting of both surfaces of web material 13, both as a sum and also separately, which will now be explained in the following with reference to two practical embodiments in FIGS. 5 and 6.

Figure 5:
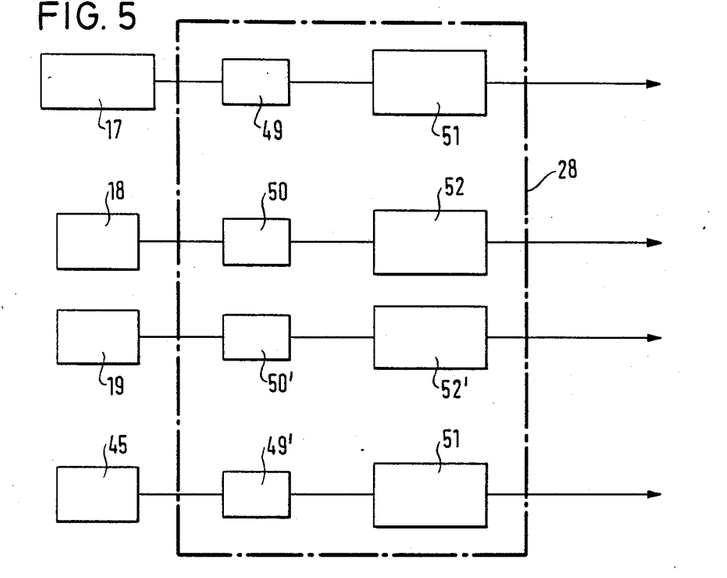

Providing the polarisation direction of the scanning beam 14 in FIG. 4 extends parallel to the scanning plane 11 and to the surface of the material 13 the following errors can be determined with the arrangement of FIG. 5:

The sum of the flatness errors of the upper and lower surfaces of the material 13 at the position of light incidence can be determined by means of the light receiving arrangement 17 via the low pass filters 49 and the position sensitive detector circuit 51. This fault determination corresponds to the upper switching stage in FIG. 3.

The light receiving arrangement 18 transmits a signal via a recursive filter 50 to a fault detector circuit 52 at the output of which there appears a signal representative of local defects in the material 13.

Alternatively, or at the same time, the electrical output signal of the light receiving arrangement 19 can be applied via a recursive filter 50 to a further fault detector circuit 52' and a signal appears at its output which is representative of local defects which make themselves noticible in transmission.

The output signal of the light receiving arrangement 45 is applied via a low pass filter 49' to a position sensitive detector circuit 51, at the output of which there appears a signal, in similar manner to the bottom of FIG. 3, which is representative for wedge errors of the material 13 at the position of light incidence.

If the polarisation direction of the scanning beam 14 is continuously switched to and fro in the manner shown in FIG. 2 between the two directions of polarisation perpendicular and parallel to the scanning plane 11 then a circuit in accordance with FIG. 6 is expedient.

The upper part of the block circuit diagram has already been described in connection with FIG. 2. In addition the output signal of the light receiving arrangement 18 is applied in the embodiment of FIG. 4 via the recursive filter 50 and the fault detector circuit 52, and the signal of the light receiving arrangement 19 of the same embodiment is applied via a recursive filter 50' to fault detector circuit 52'; in order to additionally detect local defects of the material to which the relevant light receiving arrangements respond, analogously to the two middle circuits of FIG. 5.

I claim:

1. An optical scanning apparatus for transparent, plate-like material having a surface, a normal thereto and an upper side and a lower side, said apparatus comprising:

a light source;

means for producing linearly polarized light;

a light deflecting device for generating a scanning beam for executing a periodic scanning movement in a scanning plane extending obliquely to the surface of the material at the brewster angle relative to the normal, the scanning beam generating a scanning light bead on the surface of the material;

photoelectric light receiving means disposed at an angle of reflection for differentially detecting light reflected from the upper side and from the lower side of the material including a position sensitive photo receiver for determining angular deviations between the beams reflected from the upper side and from the lower side of the material; and wherein said means for producing linearly polarized light polarizes the light alternately parallel to and perpendicular to the scanning plane.

2. The optical scanning apparatus as defined by claim 1 wherein said scanning beam for executing movement is generated by a first scanning beam having a scanning line in a first scanning plane and wherein said apparatus further comprises means for generating a second scanning beam, executing a scanning movement in a steeper scanning plane than said first scanning plane impinging on the scanning line, and a second photoelectric light receiving means for differentially detecting reflected light disposed at the angle of reflection of said second scanning beam.

3. The optical scanning apparatus as defined by claim 2 including a partially transmitting mirror wherein said first and second scanning beams are both generated by said partially transmitting mirror from said light source and said light deflecting device.

4. The optical scanning apparatus as defined by claim 1 wherein said light receiving device includes a plurality of photoreceivers aligned with respect to one another.

5. The optical scanning apparatus as defined by claim 4 wherein each of said photoreceivers is disposed as a linear array extending in a direction of the reflection displacement.

6. The optical scanning apparatus as defined by claim 4 wherein each of said photoreceivers is disposed as an areal array extending perpendicular to the direction of the reflection displacement.

* * * * *